United States Patent
Luongo et al.

(10) Patent No.: US 8,333,568 B2
(45) Date of Patent: Dec. 18, 2012

(54) DEVICE AND METHODS OF MEASURING PRESSURE

(75) Inventors: Joseph A. Luongo, Walpole, MA (US); John Angelosanto, North Attleboro, MA (US); Frank Rubino, North Attleboro, MA (US); Stanley P. Pensak, Jr., East Walpole, MA (US); David J. First, Carlisle, MA (US); Jean-Pierre Pugnaire, Arlington, MA (US); Richard R. Venable, Milton, MA (US)

(73) Assignee: Waters Technologies Corporation, Milford, MA (US)

( * ) Notice: Subject to any disclaimer, the term of this patent is extended or adjusted under 35 U.S.C. 154(b) by 832 days.

(21) Appl. No.: 10/598,310

(22) PCT Filed: Mar. 4, 2005

(86) PCT No.: PCT/US2005/006869
§ 371 (c)(1),
(2), (4) Date: Jun. 25, 2008

(87) PCT Pub. No.: WO2005/093257
PCT Pub. Date: Oct. 6, 2005

(65) Prior Publication Data
US 2008/0260558 A1    Oct. 23, 2008

Related U.S. Application Data

(60) Provisional application No. 60/550,694, filed on Mar. 5, 2004.

(51) Int. Cl.
F04B 49/00    (2006.01)

(52) U.S. Cl. .............................. 417/63; 417/437; 92/5 R

(58) Field of Classification Search .................. 417/437, 417/63, 559; 73/168, 726; 92/5 R; 91/1
See application file for complete search history.

(56) References Cited

U.S. PATENT DOCUMENTS
3,498,123 A    3/1970  Tsuchiya et al.
(Continued)

FOREIGN PATENT DOCUMENTS
JP    200628272    4/1994
(Continued)

OTHER PUBLICATIONS

Translation of Notice of Rejection (2nd Official Action) for Japanese Patent Application No. 2007-501968, Drafting Date: Dec. 21, 2011.

(Continued)

*Primary Examiner* — Devon Kramer
*Assistant Examiner* — Ryan Gatzemeyer
(74) *Attorney, Agent, or Firm* — Waters Technologies Corp

(57) ABSTRACT

Embodiments of the present invention are directed to method and devices for measuring the pressure of a pump chamber in which no internal opening or connections are needed. One embodiment of the present invention is directed to an apparatus for pumping fluid. The apparatus comprises at least one housing having a transducer surface. The transducer surface has a thickness exhibiting measurable deformation upon the chamber holding a fluid under pressure such that the transducer surface has a first position at which the chamber is at one pressure and a second position at which the chamber is at a second pressure. A strain sensor is affixed to the transducer surface producing; at least one signal upon the transducer surface assuming the first position and at least one signal upon the transducer surface assuming the second position to function as an integrated pressure transducer.

9 Claims, 3 Drawing Sheets

U.S. PATENT DOCUMENTS

| | | | |
|---|---|---|---|
| 3,724,274 A * | 4/1973 | Millar | 73/726 |
| 3,847,507 A * | 11/1974 | Sakiyama et al. | 417/22 |
| 4,058,178 A * | 11/1977 | Shinohara et al. | 177/146 |
| 4,398,427 A * | 8/1983 | Pan | 73/784 |
| 4,450,811 A * | 5/1984 | Ichikawa | 123/406.37 |
| 4,606,312 A * | 8/1986 | Nakano et al. | 123/198 DB |
| 4,775,816 A * | 10/1988 | White et al. | 310/338 |
| 4,860,639 A * | 8/1989 | Sakaguchi | 92/5 R |
| 5,163,660 A * | 11/1992 | Yamaoka et al. | 267/136 |
| 6,216,581 B1 * | 4/2001 | Murao et al. | 92/5 R |
| 6,609,883 B2 * | 8/2003 | Woodard et al. | 415/107 |
| 7,656,305 B2 * | 2/2010 | Kennedy | 340/665 |
| 2011/0005387 A1 * | 1/2011 | Ehre et al. | 92/5 R |

FOREIGN PATENT DOCUMENTS

| | | |
|---|---|---|
| JP | 2006101634 | 4/1994 |
| JP | 08-110279 A | 4/1996 |
| JP | 10-159485 A | 6/1998 |
| JP | 2002048073 | 2/2002 |
| JP | 2002228533 | 8/2002 |
| WO | WO 2005042064 A1 * | 5/2005 |

OTHER PUBLICATIONS

Japanese Translation of Notice of Rejection (Official Action), Japanese Patent Application No. 2007-501968, mailing date of Feb. 8, 2011.

United Kingdom Patent Application No. GB0614330.9, Examination Report, mailing date of Jul. 21, 2008.

United Kingdom Patent Application No. GB0614330.9, Examination Report, mailing date of Apr. 7, 2008.

* cited by examiner

DEVICE AND METHODS OF MEASURING PRESSURE

CROSS REFERENCE RELATED APPLICATION INFORMATION

This application claims priority from U.S. Provisional Patent Application No. 60/550,694, filed Mar. 5, 2004. The contents of these applications are incorporated herein by reference.

FIELD OF THE INVENTION

This invention relates to pumps and methods of measuring pressure within a pump chamber.

BACKGROUND OF THE INVENTION

It is desirable to measure the pressure inside a pump chamber. In some fields, pumps have decreased in size such that the placement of stress gauges on the housing of the pump has become difficult. For example, for pumps used in liquid chromatography it is desirable to operate at pressures greater than 3,000 pounds per square inch (psi). This pressure represents the normal upper limit of conventional chromatographic apparatus. Pressures in the ultra pressure region of greater than 4,000 up to 12,000 psi are desired. To attain these high pressures pump chambers are machined with greater precision. There is less area in the pump chamber to receive connections to pressure sensors.

SUMMARY OF THE INVENTION

Embodiments of the present invention are directed to method and devices for measuring the pressure of a pump chamber in which no internal opening or connections are needed. One embodiment of the present invention is directed to an apparatus for pumping fluid. The apparatus comprises at least one housing. The housing has an exterior surface and an interior surface. The interior surface defines a chamber for receiving a plunger and having a fluid input opening and a fluid discharge opening extending between said interior and exterior surfaces. The chamber has a cylindrical shape with a first end wall and a plunger opening for receiving a plunger. The exterior surface of the housing has a transducer surface surface define a first thickness and a second thickness. The transducer surface has the second thickness exhibiting measurable deformation upon the chamber holding a fluid under pressure such that the transducer surface having a first position at which the chamber is at one pressure and a second position at which the chamber is at a second pressure. A plunger is received in the plunger opening for reciprocating movement in the chamber. The reciprocating movement causing fluid movement, to enter the chamber through the fluid input opening and out through the fluid discharge opening. At least one strain sensor is affixed to the transducer surface. The strain sensor producing at least one signal upon the transducer surface assuming the first position and at least one signal upon the transducer surface assuming the second position to function as an integrated pressure transducer.

Preferably, the transducer surface is a flat surface capable of deformation upon pressurization of said chamber.

Preferably, the housing has a composition selected from the metals and metal alloys consisting of titanium, aluminum, and vanadium. A most preferred metal and metal alloy is titanium, aluminum and vanadium alloy, 6A14V.

Preferably, the exterior surface of the housing has a cylindrical portion and a half cylindrical portion. The cylindrical portion forms a base for attachment to other apparatus. Such other apparatus normally would consist of pump motors and supporting structure for holding the pump within a frame or further housing. The half cylindrical portion has a flat planar surface and a half cylindrical surface. The half cylindrical portion and the cylindrical portion can also be made as separate units and joined into a unitary structure. The two separate pieces can be made of different materials. It is useful to make the unit or portion having the transducer surface of the titanium alloy. For cost considerations, it may be useful to make the base unit of stainless steel.

Preferably, the transducer surface is a bottom surface of a cavity in said flat planar surface. That is a, a cavity is machined into the flat surface to provide a transducer surface. The cavity provides a second thickness, the thickness subject to deformation, of approximately 0.10 to 0.001 inches, more preferred, approximately 0.05 to 0.005 inches, and, more preferred, 0.040 to 0.01 inches. In one preferred embodiment, the cavity provides a second thickness of 0.029 plus or minus 0.001 inches.

Circuits and the like which amplify the signal of the strain sensor are preferably mounted on the flat planar surface. The circuits and strain sensor are preferably covered by a cover for protection.

A further embodiment of the present invention is directed to a method of measuring pressure in a pump chamber. The method comprises the steps of providing at least one housing having an exterior surface and an interior surface. The interior surface defines a chamber for receiving a plunger. The housing further has a fluid input opening and a fluid discharge opening extending between said interior and exterior surfaces. The chamber having a cylindrical shape with a first end wall and a second end wall. At least one end wall has a plunger opening for receiving a plunger. The exterior surface of the housing has a transducer surface between the first end wall and the second end wall. The interior surface and exterior surface define a first thickness and a second thickness. The transducer surface having the second thickness and exhibiting measurable deformation upon the chamber holding a fluid under pressure such that the transducer surface has a first position at which the chamber is at one pressure and a second position at which said chamber is a second pressure. A plunger is received in the plunger opening for reciprocating movement in the chamber. The reciprocating movement causing fluid movement to enter the chamber through the fluid input opening and out through the fluid discharge opening. At least one strain sensor is affixed to the transducer surface, The strain sensor produces at least one signal upon said transducer surface assuming the first position and at least one signal upon the transducer surface assuming the second position to function as a integrated pressure transducer. The method further comprising the step of taking readings of the strain sensor as an indication of pressure in the chamber.

These and other features and advantages will be apparent upon reading the following detailed description of the invention and viewing the drawing.

DETAILED DESCRIPTION OF THE INVENTION

The present invention will be described as a method and device for measuring the pressure of a pump chamber in which no internal opening or connections are needed. The invention has special application to pumps used in chromatography and chemical analysis. However, individuals skilled in the art will recognize that the present invention has applications in other fields as well. Individuals skilled in the art will further recognize that the present invention is subject modifications and alterations without deviating from the overall teaching of the present discussion which by way of example, without limitation discloses one or more preferred embodiments.

Figure 1:
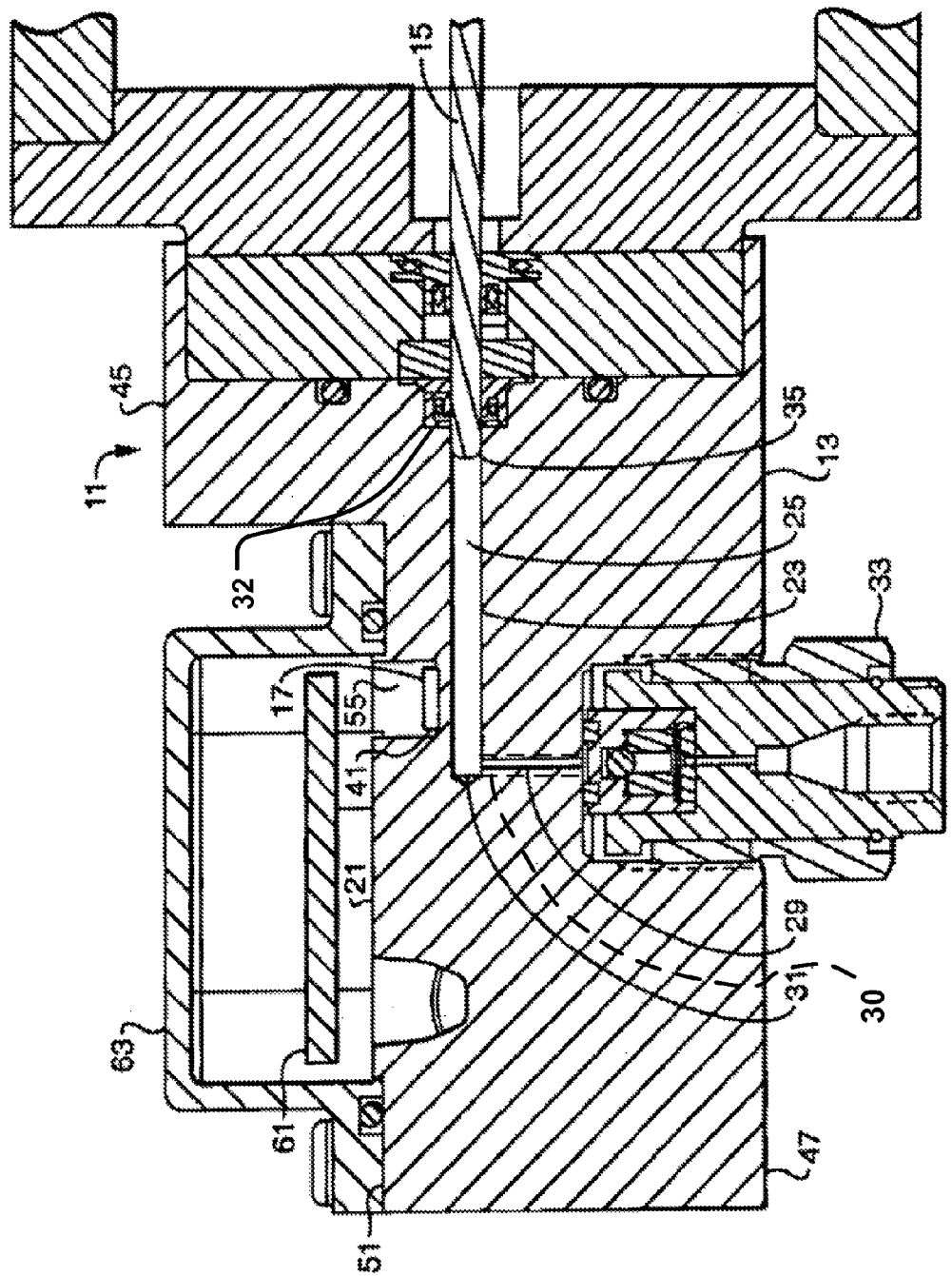
FIG. 1 depicts in cross section a side view of an apparatus embodying features of the present invention.

Turning now to FIG. 1, an apparatus, generally designated by the numeral 11, is depicted. Apparatus 11 is for pumping fluid. Apparatus 11 comprises at least one housing 13, a plunger 15 and a strain sensor 17.

Housing 13 has an exterior surface 21 and an interior surface 23. The interior surface defines a chamber 25 for receiving the plunger 15. A fluid input opening 29 and a fluid discharge opening 30 extends between said interior surface 23 and exterior surfaces 21. A check valve 33 is depicted in communication with the fluid input opening 29. The fluid outlet opening would normally have fittings for communication with other assemblies and conduits in a manner well known in the art.

The chamber 25 has a cylindrical shape with a first end wall 31 and a second end wall 32 having a plunger opening 35 for receiving plunger 15. Individuals skilled in the art will recognize that the chamber may deviate from a perfect cylinder and encompass forms with one or more sides while retaining the function of cooperation with the plunger 15. Plunger 15 is received in the plunger opening 35 for reciprocating movement in the chamber 25. The reciprocating movement causes fluid movement. Fluid enters the chamber through the fluid input opening 29 and out through the fluid discharge opening 30.

The exterior surface 21 of housing 13 has a transducer surface 41 between the first end wall 31 and plunger opening 35. The interior surface 23 and exterior surface 21 define a first thickness and a second thickness. The first thickness is for structural integrity and minimal elasticity. The second thickness exhibits deformation upon pressure induced stress. The transducer surface 41 has a second thickness exhibiting measurable deformation upon the chamber 25 holding a fluid under pressure. That is, the transducer surface 41 has a first position at which the chamber is at one pressure and a second position at which the chamber is at a second pressure. Strain sensor 17 is affixed to the transducer surface 41. Strain sensor 17 produces at least one signal upon the transducer surface assuming the first position and at least one signal upon the transducer surface assuming the second position to function as an integrated pressure transducer.

Figure 2:
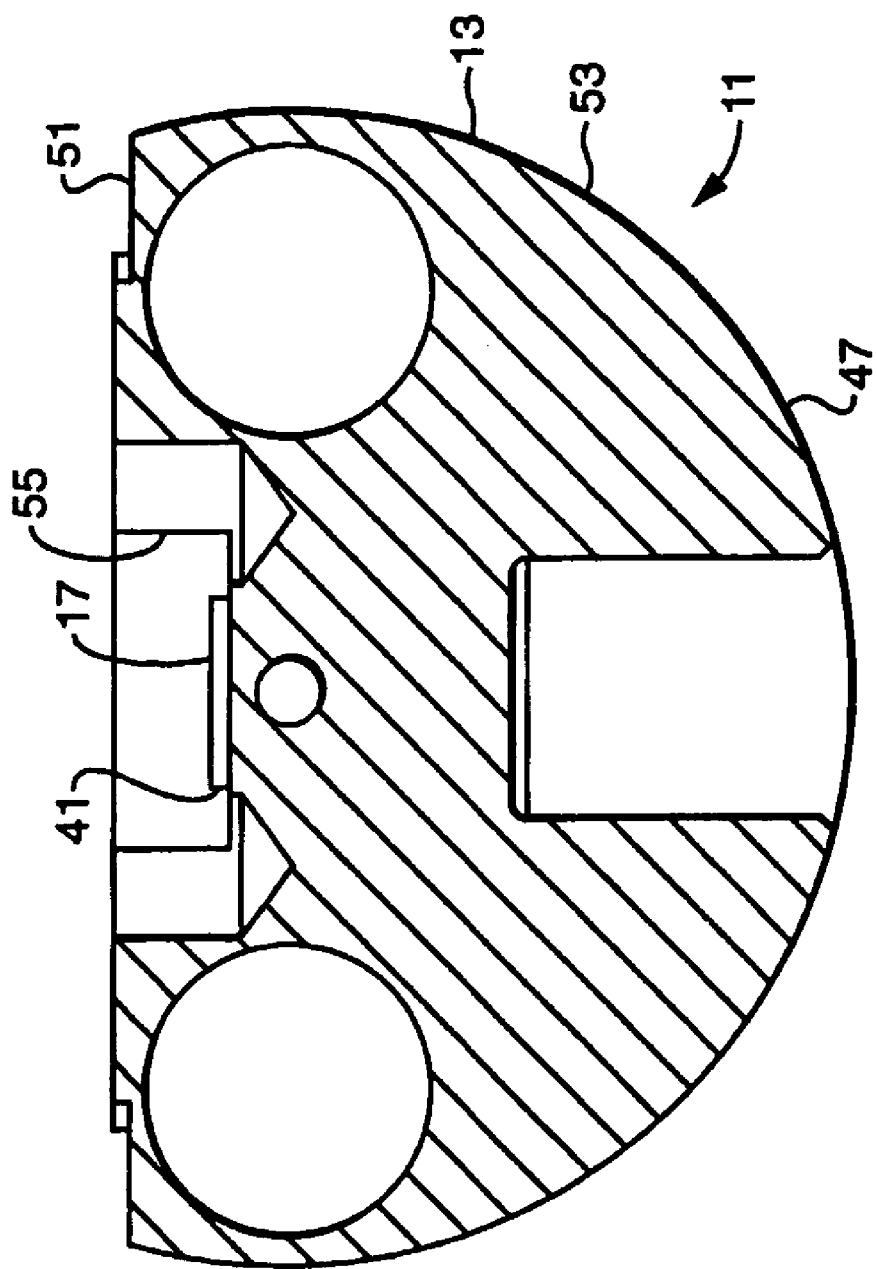
FIG. 2 depicts in cross section, an end view of an apparatus embodying features of the present invention.

As depicted in FIG. 2, the transducer surface is a flat surface capable of deformation upon pressurization of said chamber. However, curved or irregular surfaces can be used with appropriate strain sensors 17.

Housing 13 has a composition selected from the metals and metal alloys consisting of titanium, aluminum, and vanadium. A most preferred metal and metal alloy is titanium, aluminum and vanadium alloy, 6A14V.

Preferably, the exterior surface 21 of housing 11 has a cylindrical portion 45 and a half cylindrical portion 47. The cylindrical portion 45 forms a base for attachment to other apparatus (not shown). Such other apparatus normally would consist of pump motors and supporting structure for holding the pump within a frame or further housing.

Figure 3:
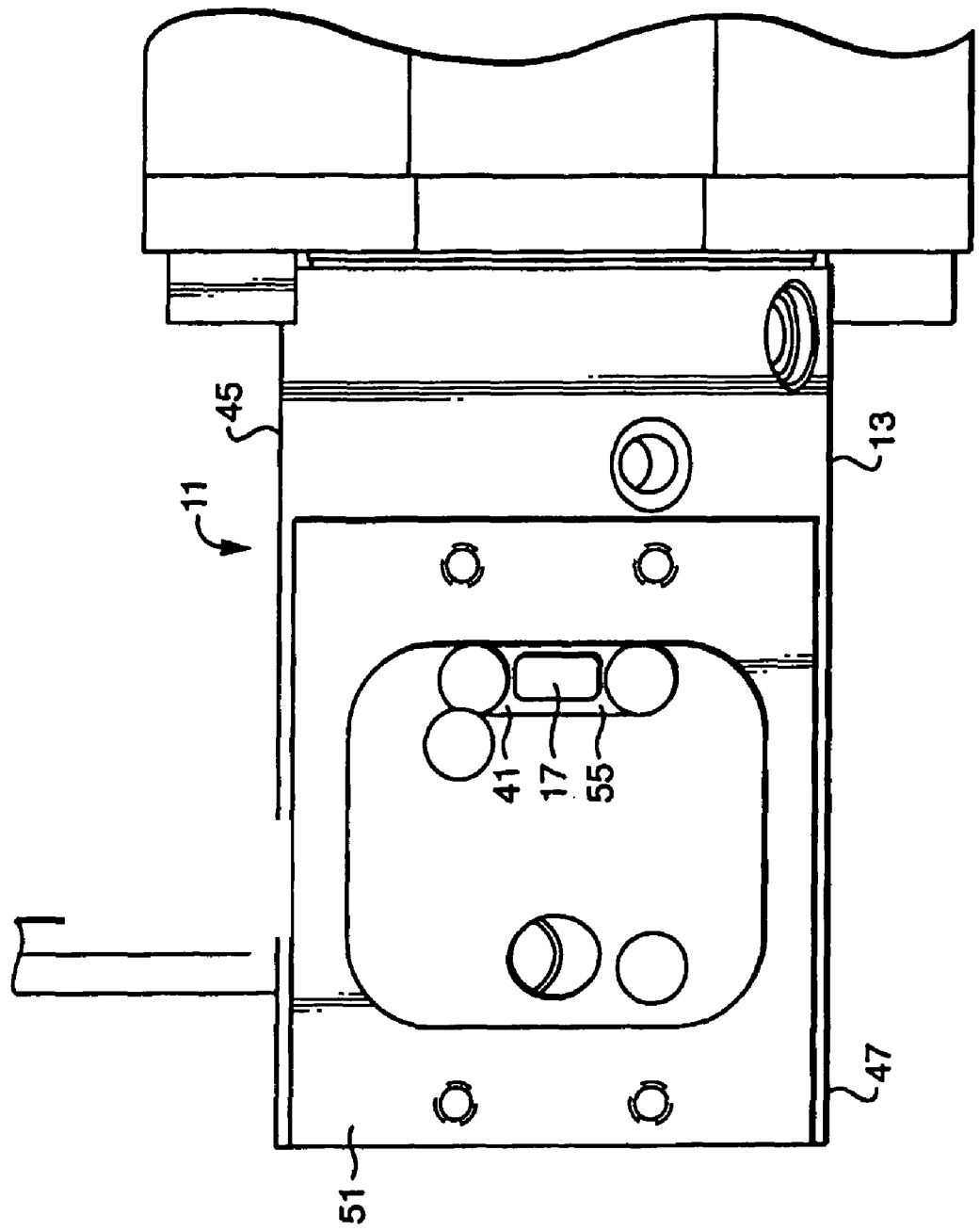
FIG. 3 depicts in top view, an apparatus embodying feature of the present invention.

As best seen in FIGS. 2 and 3, the half cylindrical portion 47 has a flat planar surface 51 and a half cylindrical surface 53. As used herein, the term "half" is used to mean part cylindrical and not a precise division. Turning now to FIGS. 1 and 2, the half cylindrical portion 47 and the cylindrical portion 45 can also be made as separate units and joined into a unitary structure. The two separate pieces can be made of different materials. It is useful to make the unit or portion having the transducer surface of the titanium alloy. For cost considerations, it may be useful to make the base unit, that is the cylindrical portion 45 of stainless steel.

Preferably, the transducer surface 41 is a bottom surface of a cavity 55 in the flat planar surface 51. That is a, cavity 55 is machined into the flat surface to provide a transducer surface 41. The cavity 55 provides a second thickness, the thickness subject to deformation, of approximately 0.10 to 0.001 inches, more preferred, approximately 0.05 to 0.005 inches, and, more preferred, 0.040 to 0.01 inches. In one preferred embodiment, the cavity 55 provides a second thickness of 0.029 plus or minus 0.001 inches.

Circuits and the like which amplify the signal of the strain sensor 17 are incorporated on a circuit board 61 and mounted on the flat planar surface. The circuit board 61 and strain sensor 17 are preferably covered by a cover 63 for protection.

A further embodiment of the present invention is directed to a method of measuring pressure in a pump chamber 25. The method comprises the steps of providing a housing 13 having an exterior surface 21 and an interior surface 23. The interior surface 23 defines a chamber 25 for receiving a plunger 15. The housing 13 further has a fluid input opening 29 and a fluid discharge opening 30 extending between said interior surface 23 and exterior surface 23. The chamber 25 has a cylindrical shape with a first end wall 31 and a plunger opening 35 for receiving plunger 15. The exterior surface 21 of the housing 13 has a transducer surface 41 between the first end wall 31 and the plunger opening 35. The interior surface 21 and exterior surface 23 define a first thickness and a second thickness. The transducer surface 41 having the second thickness and exhibiting measurable deformation upon the chamber 25 holding a fluid under pressure such that the transducer surface 41 has a first position at which the chamber is at one pressure and a second position at which said chamber 25 is a second pressure. A plunger 15 is received in the plunger opening 35 for reciprocating movement in the chamber 25. The reciprocating movement causes fluid movement. Fluid enters the chamber 25 through the fluid input opening 29 and out through the fluid discharge opening 30. At least one strain sensor 17 is affixed to the transducer surface 41. The strain sensor 17 produces at least one signal upon said transducer surface 41 assuming the first position and at least one signal upon the transducer surface 41 assuming the second position to function as a integrated pressure transducer. The method further comprising the step of taking readings of the strain sensor 17 as an indication of pressure in said chamber.

Thus, embodiments of the present invention and how to make and use the invention have been described with the understanding that the description is that of preferred embodiments subject to change and variation. And, the invention should not be so limited to such description but should encompass the subject matter of the following claims.

The invention claimed is:

1. An apparatus for pumping fluid comprising:

a housing having an exterior surface and an interior surface, the interior surface defining a cylindrical chamber having a first end wall and a second end wall, the second end wall having a plunger opening through which a plunger is reciprocal in the chamber to cause fluid to enter the chamber through a fluid inlet opening and to discharge fluid from the chamber through a fluid discharge opening, wherein the housing has an integrally formed cavity recessed into its exterior surface to provide a transducer surface which is radially spaced from the interior surface of the housing and which is disposed between said first end wall and the end of the plunger when the plunger is at a maximum displacement of a compression stroke, and wherein a strain sensor is affixed to the transducer surface to measure deformation of the housing resulting from differences in fluid pressure within the chamber, the strain sensor producing a first signal indicative of the transducer surface assuming a first position when the chamber is at low pressure and producing a second signal indicative of the transducer surface assuming a second position when the chamber is at high pressure.

2. The apparatus of claim 1 wherein the transducer surface is a flat bottom surface of the cavity.

3. The apparatus of claim 1 wherein said housing has a composition selected from the metals and metal alloys consisting of titanium, aluminum, and vanadium.

4. The apparatus of claim 1 wherein said housing has a composition comprising metal alloy 6A14V.

5. The apparatus of claim 1 wherein said exterior surface of said housing has a cylindrical portion and a half cylindrical portion, said cylindrical portion forming a base for attachment to other apparatus, said half cylindrical portion having a flat planar surface and a half cylindrical surface.

6. A method of measuring pressure in a pump chamber comprising the steps of providing a housing according to claim 1 and taking readings of the strain gauge as an indication of pressure in said chamber.

7. The apparatus of claim 5, wherein the transducer surface is radially spaced from the axis of reciprocation of the plunger.

8. The apparatus of claim 5, wherein the transducer surface is arranged substantially parallel to the axis of reciprocation of the plunger.

9. The apparatus claim 1, wherein the half cylindrical portion and the cylindrical portion are integral.

* * * * *